US00PP21740P2

(12) United States Plant Patent
Westphal

(10) Patent No.: US PP21,740 P2
(45) Date of Patent: Mar. 1, 2011

(54) ***CLEMATIS* PLANT NAMED 'DORAMI'**

(50) Latin Name: *Clematis patens×lanuginosa*
Varietal Denomination: Dorami

(76) Inventor: Friedrich Westphal, Prisdorf (DE)

( * ) Notice: Subject to any disclaimer, the term of this patent is extended or adjusted under 35 U.S.C. 154(b) by 0 days.

(21) Appl. No.: 12/584,564

(22) Filed: Sep. 8, 2009

(51) Int. Cl.
*A01H 5/00* (2006.01)

(52) U.S. Cl. ..... Plt./228
(58) Field of Classification Search ..... Plt./228
See application file for complete search history.

*Primary Examiner*—Susan B McCormick Ewoldt

(57) ABSTRACT

A new and distinct *Clematis* cultivar named 'Dorami' is disclosed, characterized by very compact plant growth and continuous flowering from May through September, with flower buds continuously produced from the leaf axils. Flowers are distinctively Violet-Blue in color. The new cultivar is a *Clematis,* suitable for ornamental garden purposes.

1 Drawing Sheet

Figure 1:
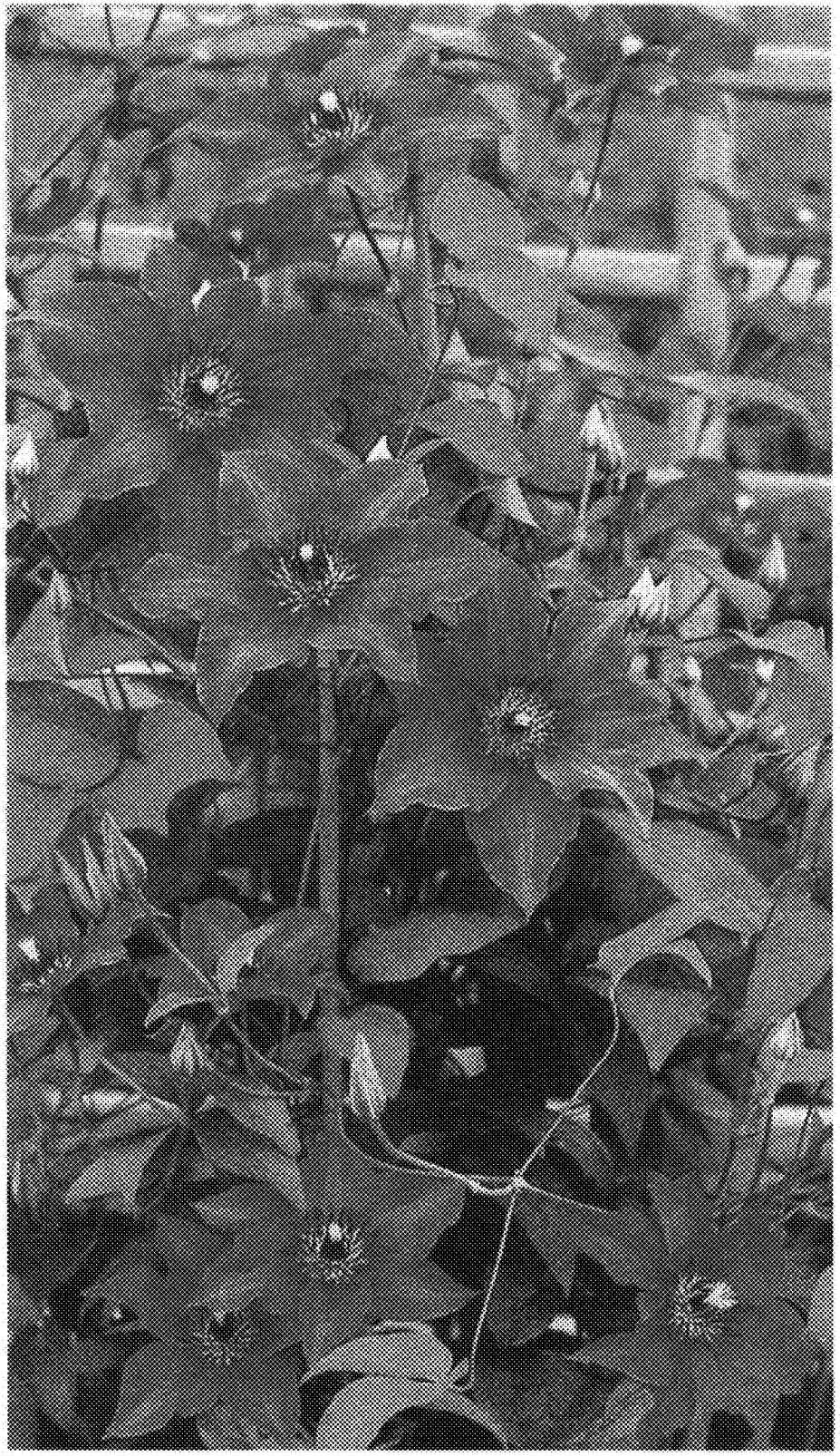

Latin name of the genus and species: *Clematis patens× lanuginosa.*

Variety denomination: 'DORAMI'.

BACKGROUND OF THE INVENTION

The new cultivar is a product of a planned breeding program conducted by the inventor in June 2006. In 2006, the inventor, Friedrich Manfred Westphal, a citizen of Germany, organized a group of unnamed, unpatented *Clematis lanuginosa* varieties to open pollinate the seed parent, the unpatented variety *Clematis patens* 'The President.' Seeds originating from this crossing were planted out, and the new variety was selected in late 2007. All work was conducted at a commercial nursery in Pinneberg, Germany.

During 2008 and 2009 the inventor propagated 'Dorami' by vegetative cuttings at the commercial nursery in Pinneberg, Germany. Subsequent generations have shown that the unique features of this cultivar are stable and reproduced true to type.

SUMMARY OF THE INVENTION

The cultivar 'Dorami' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'Dorami' These characteristics in combination distinguish 'Dorami' as a new and distinct *Clematis* cultivar:

1. Very compact plant growth.
2. Continuous flowering from May through September.
3. Distinctive violet blue color.
4. Flower buds produced continuously from the leaf axils.

COMPARISON TO PARENT VARIETY

Plants of the new cultivar 'Dorami' are similar to plants of the seed parent; *Clematis patens* 'The President' in most horticultural characteristics, however, plants of the new cultivar 'Dorami' are shorter and more compact. Additionally, plants of 'Dorami' flower continuously from May through September, whereas 'The President' flowers May and June, stops flowering, then produces another flush of flowers in August or September. Flower color of 'The President' is also darker than that of 'Dorami.'

COMMERCIAL COMPARISON

'Dorami' can be compared to the well known, unpatented commercial variety 'Elsa Spath.' While 'Dorami' and 'Elsa Spath' are similar in most horticultural characteristics, as both produces short plants, with a similar flower color, plants of 'Dorami' differ in having different shaped tepals. Additionally, plants of 'Jenmar' are overall shorter, by approximately 40 to 50 cm, and flower continuously all Summer, compared to plants of 'Elsa Spath' which consistently stop blooming during the summer, then rebloom during the Fall. Additionally, flowers of 'Dorami' are larger than flowers produced by 'Elsa Spath,' especially during the reblooming Fall period, when 'Elsa Spath' produces much smaller flowers.

'Dorami' can also be compared to *Clematis* 'Jenmar' filed concurrently with the USPTO, having Ser. No. 12/584,563. The varieties are similar in most horticultural characteristics, however, plants of 'Dorami' are shorter, with significantly less tepals per flower than 'Jenmar.' Dorami' typically produces flowers with 6 to 8 tepals, whereas flowers of 'Jenmar' have 50 to 100 tepals, forming a significantly different appearance to the inflorescence.

BRIEF DESCRIPTION OF THE PHOTOGRAPH

The accompanying photograph in FIG. 1 illustrates in full color a close up of typical foliage and flowers of 'Dorami' grown outdoors in Germany The plant is approximately 1 year old, and is planted in the ground. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used.

The following observations and measurements describe 'Dorami' plants grown in a greenhouse in Pinneberg, Germany. Plants are approximately 1 year old, in a 1 liter nursery container. The greenhouse is unheated and unshaded. Temperatures ranged from 2° C. to 20° C. at night to 5° C. to 35° C. during the day. Measurements and numerical values represent averages of typical plant types.

Botanical classification: *Clematis patens×lanuginosa* 'Dorami'.

PROPAGATION

Time to rooting: Initiation: Approximately 22 days in the Summer at approximately 24° C. to 25° C. Rooted cuttings production: Approximately 70 days in the Summer at approximately 20° C. to 28° C.

Root Description: Fine, fibrous.

PLANT

Growth habit: Climbing vine.

Height: Approximately 180 cm, measured from the soil line of the pot after approximately 1 year.

Plant spread: Approximately 50 cm after approximately 1 year.

Growth rate: Rapid. During active growing season in Spring, approximately 40 cm per month.

Branching characteristics: One main stem, and 1 to 5 lateral branches.

Length of main stem: Approximately 150 cm.

Diameter of main stem: Approximately 0.3 cm.

Main stem color: Near RHS Green 139A.

Main stem texture: Slightly pubescent.

Internode length: Varies from 6 to 18 cm.

Strength: Strong, flexible, semi-woody.

FOLIAGE

Leaf:

*Type.*—Simple.

*Arrangement.*—Opposite.

*Leaves per lateral branch.*—Average 4 to 8.

*Average length.*—Approximately 5 to 8 cm.

*Average width.*—Approximately 3 to 5 cm.

*Shape of blade.*—Heart shaped.

*Apex.*—Acute.

*Base.*—Cordate.

*Attachment.*—Petioled.

*Margin.*—Entire.

*Texture of top surface.*—Smooth.

*Texture of bottom surface.*—Smooth.

*Leaf internode length.*—Approximately 2 cm.

*Color.*—Young foliage upper side: Near RHS Green 141C. Young foliage under side: Near RHS Green 143C. Mature foliage upper side: Near RHS Green 141B. Mature foliage under side: Near RHS Green 141C.

*Venation.*—Type: Pinnate. Venation color upper side: Near RHS Green 138D. Venation color under side: Near RHS Yellow-Green 144C.

*Petiole.*—Average Length: Approximately 5 to 7 cm. Color: Near RHS Greyed-Red 180A. Diameter: Approximately 0.15 cm. Texture: Smooth.

Bloom period:

*Natural season.*—Continuously May through September.

Inflorescence type and habit: Single, axillary; flowers face mostly outward.

Rate of flower opening: Approximately 16 days from bud to fully opened flower.

Flower longevity on plant: Approximately 7 days, after fully opened. Self-cleaning.

Quantity of flowers: Free, continuous flowering, plants have at least 20 flowers at all times.

Inflorescence size:

*Diameter.*—Approximately 10 to 14 cm.

*Depth.*—Approximately 2 cm.

Corolla:

*Tepal arrangement.*—Tightly held single whorl.

*Quantity.*—Approximately 6 to 8 per flower.

*Size.*—Length: Approximately 6 cm.

*Width.*—Approximately 2.5 cm.

*Margin.*—Entire.

*Apex.*—Acute.

*Base.*—Truncate.

*Texture.*—Smooth, velvety.

Color:

*Tepals.*—When opening. Upper surface: Near RHS Violet-Blue 92B. Lower surface: Near RHS Violet-Blue 93D.

*Fully opened.*—Upper surface: Near RHS Violet-Blue 96A. Lower surface: Near RHS Violet-Blue 96C.

*Ageing.*—Upper Surface: Near RHS Violet-Blue 94C. Lower Surface: Near RHS Violet-Blue 94D.

Bud:

*Shape.*—Ovate.

*Length.*—Approximately 2 to 4 cm.

*Diameter.*—Approximately 0.5 cm.

*Color.*—Mainly Near RHS Violet-Blue 92D with base flushed Violet-Blue 92A.

Pedicels:

*Length.*—Approximately 8 cm.

*Width.*—Approximately 0.25 cm.

*Angle.*—Average 70°.

*Strength.*—Strong, flexible.

*Color.*—Near RHS Violet 84C.

Fragrance: None.

REPRODUCTIVE ORGANS

Stamens:

*Number.*—Approximately 80 to 100 per flower.

*Anther length.*—0.8 cm.

*Anther color.*—Near RHS Violet 86A.

*Anther shape.*—Oblong.

*Pollen quantity.*—Not observed to date.

*Filament length.*—Approximately 1.8 cm.

*Filament aspect.*—Straight.

*Filament color.*—Near RHS White N155B near base, upper end near Violet 86D.

Pistil:

*Number.*—Approximately 50 to 70 per flower.

*Length.*—Approximately 1 cm.

*Style color.*—Near RHS White 155B.

*Style length.*—Approximately 1 cm.
*Stigma.*—Shape: Linear. Color: Near RHS White 155B.

OTHER CHARACTERISTICS

Seeds and fruits: Not observed to date.
Disease/pest resistance: Neither resistance nor susceptibility to pathogens and pests common to *Clematis* have been observed.
Temperature tolerance: Tolerates temperatures from approximately −20 ° C. to 45° C.

What is claimed is:

1. A new and distinct cultivar of *Clematis* plant named 'Dorami' as herein illustrated and described.

* * * * *